US009989443B2

(12) United States Patent
Knox

(10) Patent No.: US 9,989,443 B2
(45) Date of Patent: Jun. 5, 2018

(54) SAMPLING POINT FOR A PARTICLE DETECTOR

(71) Applicant: Xtralis Technologies Ltd., Nassau (BS)

(72) Inventor: Ron Knox, Mount Eliza (AU)

(73) Assignee: Xtralis Technologies Ltd., Nassau, NP (BS)

( * ) Notice: Subject to any disclaimer, the term of this patent is extended or adjusted under 35 U.S.C. 154(b) by 0 days. days.

(21) Appl. No.: 14/402,748

(22) PCT Filed: May 21, 2013

(86) PCT No.: PCT/AU2013/000529
§ 371 (c)(1),
(2) Date: Nov. 21, 2014

(87) PCT Pub. No.: WO2013/173868
PCT Pub. Date: Nov. 28, 2013

(65) Prior Publication Data
US 2015/0096389 A1    Apr. 9, 2015

(30) Foreign Application Priority Data

May 21, 2012  (AU) ................................ 2012902081

(51) Int. Cl.
| G01N 1/26 | (2006.01) |
| G01N 1/22 | (2006.01) |
| G08B 17/10 | (2006.01) |
| G05D 7/06 | (2006.01) |
| G01N 33/00 | (2006.01) |
| G08B 17/113 | (2006.01) |

(52) U.S. Cl.
CPC ............. *G01N 1/2247* (2013.01); *G01N 1/26* (2013.01); *G01N 33/0009* (2013.01); *G05D 7/0676* (2013.01); *G08B 17/10* (2013.01); *G08B 17/113* (2013.01)

(58) Field of Classification Search
CPC .... G01N 1/2247; G01N 1/26; G01N 33/0009; G05D 7/0676; G08B 17/10; G08B 17/113
USPC ............................. 73/863.31, 863.33, 865.5
See application file for complete search history.

(56) References Cited

U.S. PATENT DOCUMENTS

| 3,765,247 A | * | 10/1973 | Riggs ...................... G01N 1/26 422/93 |
| 5,103,212 A | | 4/1992 | Notarianni et al. |
| 6,167,107 A | | 12/2000 | Bates |

(Continued)

FOREIGN PATENT DOCUMENTS

| CN | 201654940 U | 11/2010 |
| NL | 1016598 C2 | 5/2002 |

*Primary Examiner* — Helen Kwok
*Assistant Examiner* — Nashmiya Fayyaz
(74) *Attorney, Agent, or Firm* — Boyle Fredrickson, S.C.

(57) ABSTRACT

A sampling point for use with an aspirating particle detection system. The sampling point includes: a body; a plurality of apertures in the body for drawing an air sample from an ambient environment; an outlet for delivering the sampled air, at a predetermined sample flow rate, from the body into a sampling pipe of the network of sampling pipes; and a means for maintaining the predetermined sample flow rate regardless of the presence or absence of ambient flow of air about the body. A particle detection system, and air sampling system are also described.

11 Claims, 6 Drawing Sheets

(56) References Cited

U.S. PATENT DOCUMENTS

| | | | | |
|---|---|---|---|---|
| 8,181,504 | B2* | 5/2012 | Tewarson | G01N 1/26 73/23.41 |
| 8,776,620 | B2* | 7/2014 | Timmis | G01N 1/2214 73/863.22 |
| 2003/0033890 | A1* | 2/2003 | Rodgers | G01N 1/2211 73/863.43 |
| 2004/0145484 | A1* | 7/2004 | Wagner | G08B 17/10 340/628 |
| 2005/0087027 | A1* | 4/2005 | Widmer | G01N 1/2258 73/863.02 |
| 2006/0234621 | A1 | 10/2006 | Desrochers et al. | |
| 2007/0137318 | A1 | 6/2007 | Desrochers et al. | |
| 2009/0002182 | A1 | 1/2009 | Knox et al. | |
| 2009/0237259 | A1 | 9/2009 | Yokota | |
| 2010/0328082 | A1 | 12/2010 | Danz et al. | |
| 2012/0079871 | A1 | 4/2012 | Williamson | |
| 2013/0160571 | A1 | 6/2013 | Williamson | |
| 2015/0310717 | A1* | 10/2015 | Al-Farra | G08B 17/113 340/628 |

* cited by examiner

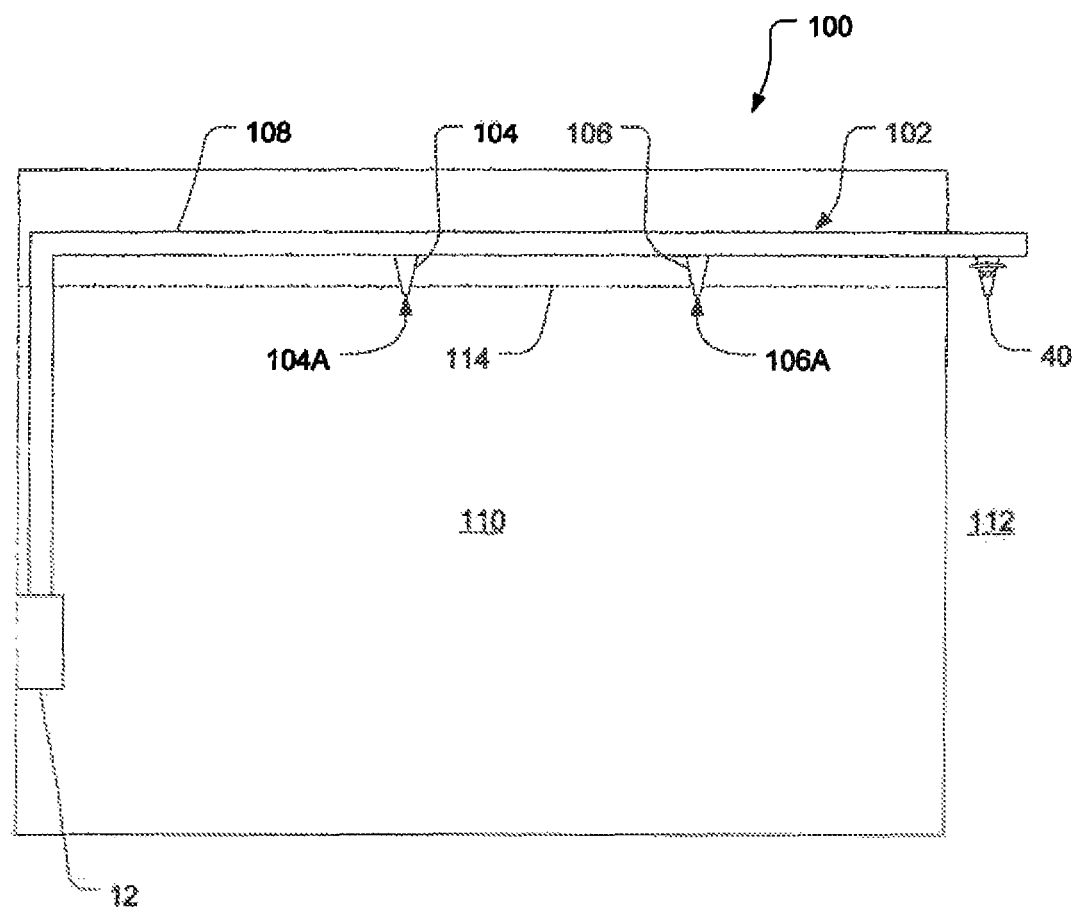

SAMPLING POINT FOR A PARTICLE DETECTOR

FIELD OF THE INVENTION

The present invention relates to a sampling point for use in a network of sampling pipes forming part of an aspirating particle detection system, and to an aspirating particle detection system, and components thereof, having such a sampling point.

BACKGROUND OF THE INVENTION

In the aspirating particle detection systems, such as the Vesda® range of smoke detectors manufactured by Xtralis Pty Ltd, a network of sampling pipes is routed over an area to be monitored by the particle detection system. FIG. 1 illustrates such a particle detection system 10. The system 10 includes the particle detector 12 coupled to a sample pipe network 14 comprised of two sampling pipes 16. Although, the network may include further sampling pipes, or conversely, a single sampling pipe. Each sampling pipe includes a plurality of air sampling points 18. The air sampling points 18 may be a simple hole in the sampling pipe 16 or a fitting that couples to the pipe 16 and has a hollow generally cylindrical frusto-conical body with a hole at the end, into which air is drawn. Such a fitting can be directly connected to the air sampling pipes, e.g. by being interposed in the pipe or attached to a T-junction directly, or connected thereto by a length of hose. In use, air is drawn into the air sample inlets 18 and into the particle detector 12 by an aspirator 20. The aspirator 20 typically forms part of the particle detector 12. Air drawn through the system 10 enters the detector at detector inlet 21 and passes, through inlet plenum 26 having a flow sensor 24, to the aspirator 20. The aspirator then outputs the air to an outlet plenum 28, from where most of the air is exhausted back to the atmosphere via an exhaust port 22. The air pressure in the outlet plenum 28 is at high pressure, compared to the air at the inlet plenum 26, so a portion of the air is fed back to the inlet plenum via (optional) dust filter 30 and particle detection chamber 32, where any particles of interest are detected.

The aspirator 20 delivers sample air drawn from the ambient air in the volume (e.g. room or cabinet etc) that is being monitored to the detector 12 at a predetermined flow rate. As will be appreciated the flow rate will vary depending on system parameters, but will typically be in the range of 10 to 150 liters per minute. FIG. 1A is a graph showing flow rate 13 delivered to the particle detector 12 vs time. During operation of the particle detection system 10, the flow rate 13 in each sampling pipe 16 and/or to the detector 12 is set by configuring the aspirator 20 to run nominally at the predetermined flow rate. However, the flow rate 13 may vary from the nominal flow rate 15a due to external environmental influences or blockages at one or more sampling point. Therefore, the flow rate is monitored by flow sensor 24 to ensure that the flow rate is within a specified allowable range. The allowable range is typically set by upper 15b and lower 15c flow thresholds, which are typically percentage deviations from the nominal 15a rate. Short transient variations in flow (having a duration less than a predetermined delay period) outside the specified range are not necessarily indicative of a problem in the sampling network and may therefore be ignored. However, if the flow rate is outside the specified range for longer than a fault delay period 17, it will be determined that the predetermined flow rate is not being met. The function or reliability of particle detector may be compromised, and a fault signal issued.

The inventors have determined that, some users of aspirating particle detection systems may wish to monitor an outside area, rather than an inside area for which such systems are generally intended. However, outside environments present a challenge in that an ambient flow of air about the sampling points, for example due to wind, can result in ambient air being pushed into, or drawn from, the sampling points, and associated sampling network, causing an increase or decrease in flow beyond the acceptable limits. Due to the localised nature of turbulence and flow speeds of ambient relative air flow between different sampling points may also become unbalanced. As illustrated in FIG. 1A, if the flow rate 13 increases beyond the acceptable range for a period 19a, less than the fault delay period 17, the predetermined flow rate is considered to be met, so no fault signal is issued. However, some time later, the flow rate 13 decreases beyond the acceptable range for a period 19b, which is longer than the fault delay period 17, the predetermined flow rate is considered to not be met, so a fault signal is issued.

The present invention addresses the above challenge in using an aspirated particle detection system in an outdoor environment.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In a first aspect of the invention there is a sampling point for a sampling pipe forming part of an aspirating particle detection system, the sampling point including:
a body; a plurality of apertures in the body for drawing an air sample from an ambient environment; an outlet for delivering the sampled air, at a predetermined sample flow rate, from the body into a sampling pipe of the network of sampling pipes; and a means for maintaining the predetermined sample flow rate regardless of the presence or absence of ambient flow of air about the body.

Preferably, the body includes a passage between the apertures and the outlet.

Preferably, the means for maintaining the predetermined sample flow rate is a specific spatial arrangement of the apertures in the body.

Preferably, the plurality of apertures are equally spaced about the body. In a preferred embodiment, there are three of said apertures, although more may be used. Preferably the body is cylindrical. Preferably, the apertures are spaced at 120 degree intervals about a central axis of the cylindrical body. Preferably, the central axis of the body is perpendicular a direction of opening of the outlet.

In an embodiment, the body includes a mounting mechanism for mounting the body to a sampling pipe of a particle detection system or support structure. The body may be directly connected to the sampling pipe or coupled to it via a dedicated pipe.

In an embodiment of the invention, the sampling point includes a weather shield configured to provide protection from water ingress or hole blockage due to rain or snow.

In a second aspect of the invention there is provided a conduit for passing air towards an particle detector in an aspirating particle detection system, the conduit including a sampling point comprised of a cluster of apertures on the conduit, the cluster of apertures being arranged such that a predetermined sample flow rate through the conduit is maintained regardless of the presence or absence of ambient air flow about sampling point.

In a third aspect of the invention there is provided a sampling pipe for delivering air to a particle detector in an aspirating particle detection system, the sampling pipe including at least one sampling point according to the first aspect of the invention.

In a fourth aspect of the invention there is provided a sampling pipe for delivering air to a particle detector in an aspirating particle detection system, the sampling pipe including a conduit according to the second aspect of the invention.

In a fifth aspect of the invention, there is provided an aspirating particle detection system including at least one sampling pipe according to the third or fourth aspects of the invention, and further including a particle detector in fluid communication with at least one sampling pipe according to the present invention, wherein the detection system includes an aspiration means for delivering air into the detector at a predetermined aspiration flow rate, the predetermined aspiration flow rate determining said predetermined sample flow rate. Preferably the aspirating means is a fan in the detector.

In a sixth aspect of the invention, there is provided an air sampling system for a particle detector, the sampling system having:
a plurality of sampling points for drawing air into the sampling system; the sampling system being configured to have a flow of air at a predetermined flow rate at a location downstream from at least some of the sampling points;
wherein at least one of the sampling points upstream from the location has an arrangement for maintaining flow rate via the sampling point into the sampling system such that the flow rate at the location is maintained at the predetermined flow rate regardless of the presence or absence of ambient flow of air about the sampling point.

In a seventh aspect the present invention provides an air sampling system for a particle detector, the air sampling system having: at least one sampling point for drawing air into the sampling system; the sampling system being configured to have a flow of air at a predetermined flow rate at a location downstream from at least one of the sampling points; wherein at least one of the sampling points upstream from the location has an arrangement for maintaining the flow of air being drawn into the sampling point at a rate that ameliorates the problem of flow faults in the detection system, in the presence of varying ambient flow about the sampling point. The arrangement can include a plurality of inlet apertures. The sampling point can be of the type described above.

In the sixth and seventh aspects of the invention, the flow rate at the location is preferably independent of the ambient flow.

Preferably, in the sixth and seventh aspects of the invention, the arrangement comprises a spatial arrangement of apertures configured as inlets for sampling ambient air.

Preferably, the sampling point also includes an outlet in fluid communication with a sampling pipe of the sampling network.

Preferably, the apertures in a sampling point are arranged to balance air flowing into its one or more apertures, due to ambient flow past the sampling point.

In this regard the apertures can be arranged to balance air flowing into one or more of the apertures due to ambient flow past the sampling point, such that the affect of a change in flow rate into one of the apertures caused by ambient flow is at least partly matched by changes in flow rate in at least one of the other apertures, so as to reduce the affect of the change in flow rate into the one aperture on total flow rate into the sampling point.

It will be appreciated this effect generally occurs in cases when the direction of ambient air flow is such that a front of ambient air flow passes one of the apertures before passing another of the apertures. This contrasts with having the direction of ambient air flow such that the front simultaneously reaches all apertures. In use, the sampling point, will generally protrude from a wall, with the apertures spaced in a plane that is parallel to the wall. It will therefore be appreciated that the entry of ambient air flow into at least one of the apertures and exit out from another of the apertures occurs for a direction of air flow that is in this same plane, or for a portion of the air flow that has a component in such a direction, as opposed to being perpendicular to the plane.

In one embodiment, the sampling point of the sixth or seventh aspects of the invention is a sampling point in accordance with the first aspect of the invention.

In another embodiment the sampling point is included on a conduit of the sampling system, wherein the conduit is in accordance with the second aspect of the invention.

The air sampling system preferably includes an aspiration-means for delivering air into particle detector at an aspiration flow rate, the aspiration flow rate determining the flow rate from the sampling point into a sampling pipe of the air sampling system. Preferably, the air sampling system further includes a sensor for determining (e.g. by measurement) air flow (e.g. air flow rate) at said location for measuring flow. Preferably, the air sampling system is configured to issue a fault signal in the event that the measured air flow is not at the predetermined flow rate. In a preferred form the system is, configured to determine that the measured flow rate is not at the predetermined flow rate f the flow rate is either outside an acceptable range of flow rates, or outside an acceptable range of flow rates for longer than an acceptable time.

In another aspect of the present invention there is provided a sampling point for a sampling pipe forming part of an aspirating particle detection system, the sampling point including: a body; a plurality of apertures in the body for enabling an air sample from an ambient environment to be drawn into the sampling point; said apertures being arranged around the body in a spatial arrangement; an outlet for delivering the sampled air from the body into a sampling pipe of a network of sampling pipes. Preferably the body includes a passage between the apertures and the output. Most preferably the apertures are equally spaced about the body. Preferably, there are three, or more, apertures. In one form the body is cylindrical and the apertures are spaced at 120 degree intervals about a central axis of the cylindrical body. The sampling point includes a shield configured to provide protection for the apertures of the sampling point, from foreign bodies.

In another aspect there is provided an aspirating particle detection system including an air sampling system of any one of the types described herein and a particle detector.

In a particularly advantageous embodiment of the invention, the particle detector is a smoke detector and the aspirating particle detection system is an aspirating smoke detection system.

BRIEF DESCRIPTION OF THE DRAWINGS

Further aspects of the present invention and further embodiments of the aspects described in the preceding paragraphs will become apparent from the following description, given by way of example and with reference to the accompanying drawings.

FIG. 5 illustrates an exemplary particle detection system including a sampling point according to an embodiment of the present invention.

DETAILED DESCRIPTION OF THE EMBODIMENTS

Figure 1:
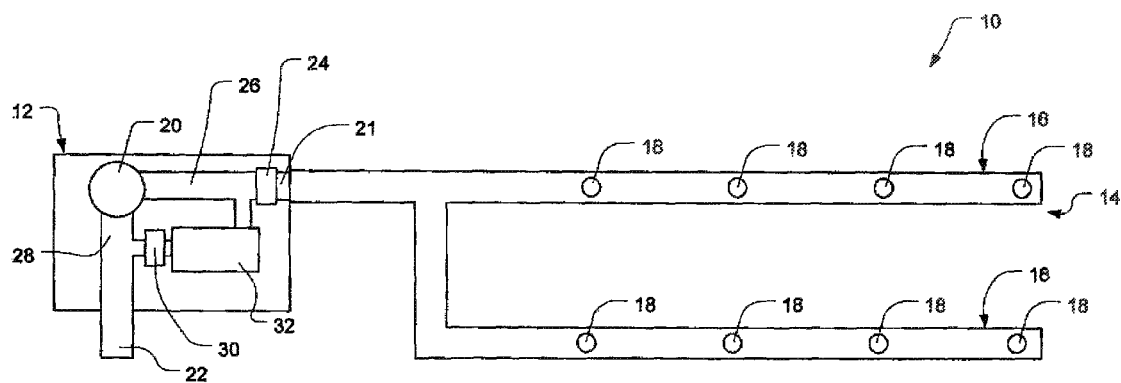
FIG. 1 shows a block diagram of an exemplary aspirated particle detection system.
Figure 1A:
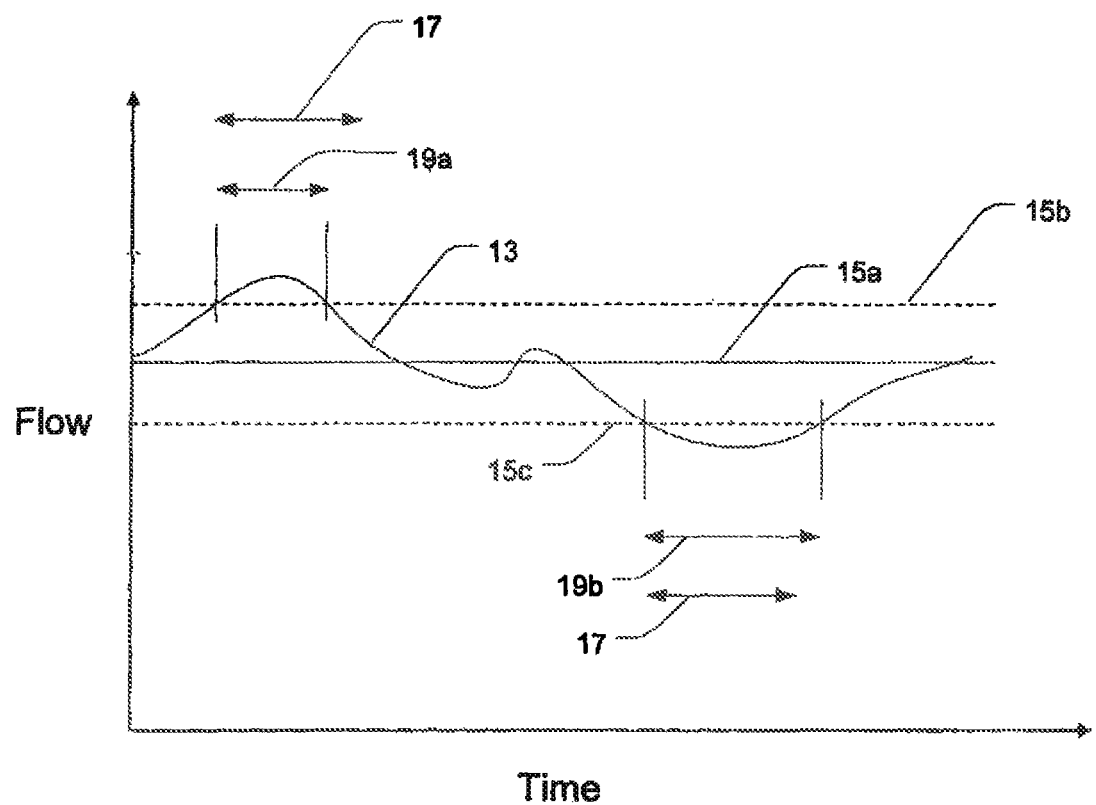
FIG. 1A is a graph showing flow rate versus time indicating limits for acceptable and unacceptable flow.
Figure 2:
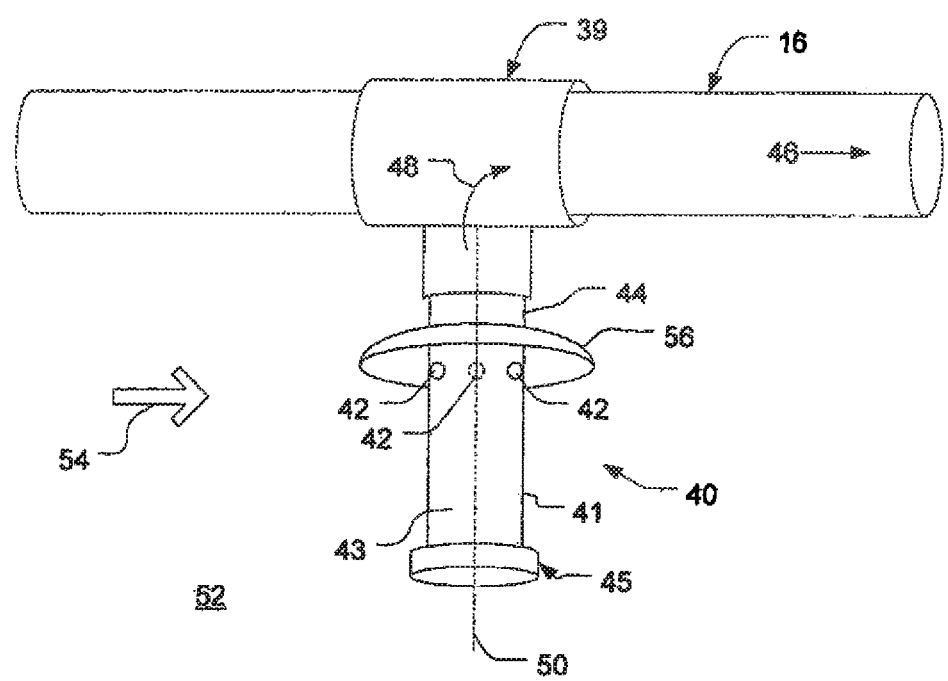
FIG. 2 shows a sampling point in accordance with the first aspect of the present invention on a sampling pipe of the particle detection system of FIG. 1.
Figure 2A:
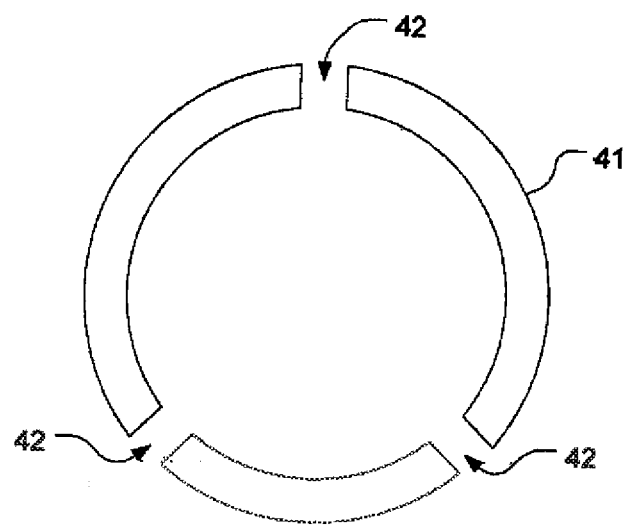
FIG. 2A shows a cross-sectional view of the sampling point of FIG. 2.

An exemplary embodiment of the present invention is an aspirating particle detector system, as in FIG. 1, but having, in lieu of sampling points 18 of FIG. 1, sampling points 40 of the present invention, as exemplified in FIG. 2.

Sampling point 40 includes a body 41 which is generally cylindrical and closed on its bottom end 43 by an end cap 45. It has three inlet apertures 42 and an outlet 44 in fluid communication with a segment of pipe 16 via tee junction adaptor 39. The body 41, being a cylindrical body, has a central axis 50, the longitudinal axis of the cylinder. The inlet apertures 42 are spaced equally about the central axis 50, thereby being spaced, at 120° intervals, as illustrated in a cross-sectional view of the body 41, cutting through each of the inlet apertures 42. The behaviour of the sampling point 40 in an outdoor environment will, now be described. The aspirator 20 draws air through the sampling network 14 and sampling pipes 16 go in at a predetermined aspiration flow rate into the detector 12. This results in the sampling point drawing air from the ambient environment 52 such that the outlet 44 of the sampling point 40 delivers sampled air to the sampling pipe at a predetermined sample flow rate.

The ambient air has an ambient flow 54 about the sampling point 40. The three inlet apertures, being of equal size and, spaced evenly about the axis 50, result in the net flow of ambient air due to the bulk flow of air about the body, to be zero. In other words, the bulk flow of air 54, e.g. due to wind, does not result in a change to the sample flow rate 48 into pipe 16 from the sampling point 40, in comparison with a static ambient environment. In the event of excessive movement of ambient air past the sampling point (e.g. windy outdoor conditions) the equal spacing of inlet apertures is intended to provide a balance in net flow between those inlet apertures that have air being forced into them by inwardly directed air movement, and inlet apertures that have air being drawn out of them by passing air causing a local low pressure zone outside inlet aperture. Clearly the net flows for all apertures may be into the sampling point, but the rate of flow in each being either increased or decreased by the influence of ambient flow (compared to the situation with no ambient flow). As will be appreciated, the balance need not be perfect, but only sufficient to allow air to be drawn into the sampling point at a rate that ameliorates the problem of flow faults in the detection system by meeting the requirements for predetermined flow rate at the detector, such that the flow rate at the detector is not outside an acceptable range, or outside an acceptable range for longer than a fault delay period of time, as noted above. Though a predetermined flow rate at the detector could alternatively or additionally be achieved by a control loop to control the aspirator based on a sensed flow, the present invention has the advantage of being entirely passive. The predetermined flow rate is achieved solely by the mechanical configuration and size of the sampling point.

The sampling point 40 includes an optional shield 56 circumferentially around the body 40. The shield is generally dome shaped, like an umbrella, extending from the body 41 to approximately the top of apertures 42, so as to avoid excessive rain or snow ingress.

When the sampling pipe 16 is connected to the detector 12 air is drawn through the pipe 16 by the aspirator. The air is drawn in direction 46, as shown in FIG. 2. This results in a predetermined sample flow rate 48 entering the pipe 16 from the sampling point 40, via outlet 44. Given a specified aspiration flow rate, the sample flow rate will be a fixed portion of the aspiration, flow rate, as determined by the geometry and dimensions of the pipe 16 and the combined network 14 of sampling pipes. In some embodiments, the sample flow rate is the sample as the flow rate through sample, pipe 46, for example in the case of only a single sampling point 40.

In the case of multiple sampling points 18 for a single sampling pipe 16, the contribution of flow from any one sampling point may be small compared to the overall flow in the sampling pipe, or to the detector (especially if there are multiple sampling pipes). Thus, it may be more important to ensure that the net flow through the sampling pipe 46, or to the detector 12 is at an acceptable level, thus allowing a greater tolerance for flow rate delivered by the sampling point 18. In this case, the effect that the balancing of apertures 42 has on dampening any ambient flow changes need not be as strong.

For a given flow rate in the sampling pipe 16, the sample flow rate at each sampling point 40 is controlled by the number of inlet apertures and the size and geometry of each aperture. However, in general, the combined cross section of each of the apertures lowers the flow impedance through each sampling point. Given that the aspirator 20 is capable of drawing a specific volume of air at the aspiration flow rate, there is a minimum flow restriction required through each sampling point, and therefore a maximum combined aperture size. Conversely, there is a maximum restriction, and corresponding minimum combined aperture size, to allow sufficient air to flow through each sampling point 40. For the Vesda® range of aspirating smoke detection systems, for example, sampling points having a single inlet aperture are specified such that the aperture diameter is between 4.5 and 6 mm. Thus, using three apertures, the combined cross section of each of the apertures is equal to that of a single 4.5-6 mm aperture, in the case where each of the three apertures has a diameter between 2.6 and 3.5 mm.

Figure 3:
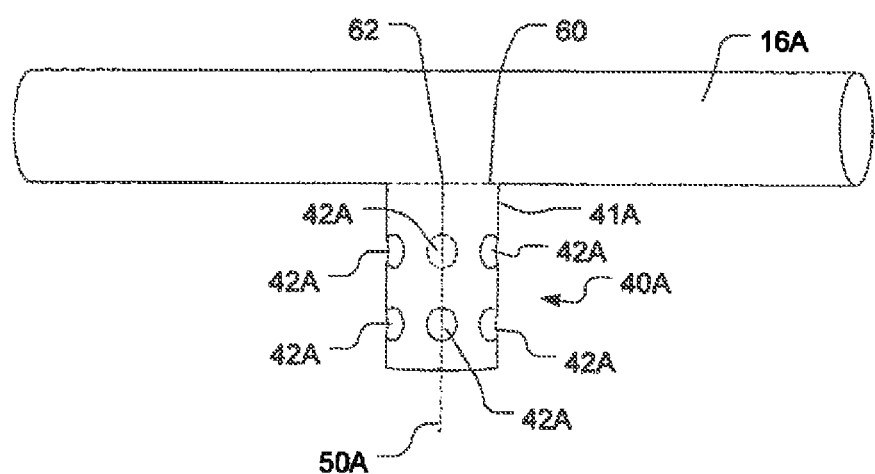
FIG. 3 shows another embodiment of a sampling point, in accordance with the present invention; and a sampling pipe of the particle detection system of FIG. 1.

In other embodiments of the invention, the sampling point can include more than 3-apertures. For example, in FIG. 3, the sampling point 40A has six apertures 42A, consisting of two groups of 3 apertures, each group being spaced equally about the central axis 50A. To keep the same combined cross section as the 3-aperture embodiment (e.g. to enable this sampling point to be used on a sampling pipe network with other sampling points of conventional design and maintain correct flow balance between the sampling points), each of the six apertures must be smaller than the apertures of the 3-aperture counterpart, although for illustrative purposes, the apertures 42A and body 41A are shown in an exaggerated size in comparison with the segment of the sampling pipe 16A.

This relative reduction in size of the sampling holes presents a problem that smaller holes are more prone to becoming blocked by dust and other objects over time. One mechanism to address this potential problem is to set each of the apertures to the same hole size as the 3 aperture embodiment, but to use a flow restrictor to control the flow impedance of the whole sampling point. In this example a restrictor 60, having an impedance defining aperture 62, is included to determine a minimum flow impedance of the sampling point 40A into the sampling pipe 16A. The restrictor 60 can either be joined directly to the sampling point 40A, be placed between the sampling point 40A and the sampling pipe 16A, or be part of the sampling pipe 16A (for example, it may be an aperture or collection of apertures in the sampling pipe 16A). However, it should be appreciated, that the impedance of the apertures 42A must still be sufficiently high that the restrictor 60 does not become totally exposed to movements of ambient air about the sampling point and therefore effectively become the only inlet aperture in the sampling point, thereby negating the balancing effect of the plurality of apertures 42A.

Figure 4:
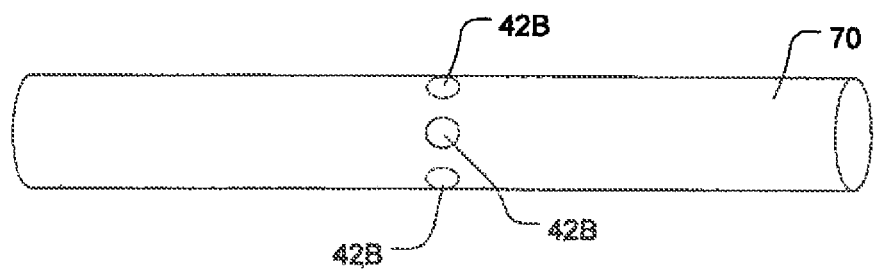
FIG. 4 shows a conduit in accordance with the second aspect of the present invention, the conduit being part of a sampling pipe of the particle detection system of FIG. 1.

Another embodiment of the invention is shown in FIG. 4, which shows a section of a conduit 70 for passing air towards a particle detector. In this embodiment the conduit 70 is a portion of pipe 16, wherein each sampling point is comprised of a cluster of apertures 42B on the conduit 70. The cluster of apertures 42B are arranged such that a predetermined sample flow rate through the conduit 70 is maintained in the presence of ambient air flow about the sampling point. As in the previous example the apertures are arranged in a ring around the conduit in equal spacing. Thus, as in the other embodiments of the present invention, the flow is the same regardless of whether there is ambient flow. Since change in ambient flow does not change the flow in the sampling network from the predetermined flow rate, the detection system can operate in the presence of wind without causing errors or a degradation of reliability.

The sampling point 40 has been described and illustrated as being integral with, or directly connected to a sampling pipe. However a sampling point according to an embodiment of the present invention may be created as a stand-alone fitting (optionally with a mounting mechanism) which is connected to the pipe network by a length of hose or similar.

FIG. 5 illustrates an exemplary particle detection system 100. The system 100 is arranged to detect particles, e.g. smoke particles, in a room 110 and in an adjacent outside space 112. The particle detector 12 is the same as the detector 12 described in connection to FIG. 1, and will not be described again. The illustrative air sampling system 102 includes three sampling points 104, 106 and 40 leading into a single air sampling pipe 108. Part of the sampling pipe 108 is concealed from view from within the room 110, by being hidden above a ceiling panel. The sampling pipe 108 leads to the particle detector 12. Air is drawn into the air sampling network 102 via an aspirator (not shown) of the particle detector 12. Sampling points 104 and 106 are conventional sampling points of the type having a single inlet 104A and 106A on the distal end of their respective sampling point bodies. Sampling points 104 and 106 are mounted to the ceiling panel 114 and arranged such that their apertures 104A, 106A are in fluid communication with the room 110.

Since the room 110 is a relatively controlled environment with relatively low levels of, ambient air flow, conventional sampling points 104 and 106 can be used. On the other hand the outside space 112 may be subject to greater variation, in ambient air flow, as might be caused by wind. Therefore, in order to minimise the affect of this varying ambient flow about the outdoor sampling point 40 on the flow rate of sample air reaching the detector the sampling point 40 is the same as that described in FIG. 2. As will be appreciated more (or fewer) sampling points may be included in a system of this kind. There is no need to include any conventional sampling points.

It will be understood that the invention disclosed and defined in this specification extends to all alternative combinations of two or more of the individual features mentioned or evident from the text or drawings. All of these different combinations constitute various alternative aspects of the invention.

The claims defining the invention are as follows:

1. An air sampling system for use with a particle detector, the sampling system having:
   at least one sampling pipe configured to deliver air to a particle detector;
   the sampling pipe being connected to a plurality of sampling points for drawing air into the sampling pipe;
   the sampling system being configured to have a flow of air at a predetermined flow rate at a location downstream from at least some of the sampling points;
   wherein at least one of the sampling points is upstream from the location downstream and has a generally cylindrical body that is closed on a bottom end and has a plurality of equally-sized apertures equally spaced about a central axis of the cylindrical body in a spatial arrangement for drawing an air sample from an ambient environment into the body, and an outlet for delivering the sampled air, at a predetermined sample flow rate, from the body into the at least one sampling pipe, the spatial arrangement of the equally-sized apertures balancing air flowing into the body such that the effect of a change in flow rate into one of the apertures caused by the presence or absence of ambient flow of air about the at least one upstream sampling point is at least partly matched by changes in flow in at least one of the other apertures, delivering the sampled air at the outlet at the predetermined sample flow rate.

2. An air sampling system in accordance with claim 1, wherein the flow rate at the location downstream is independent of the ambient flow.

3. An air sampling system in accordance with claim 1, wherein the air sampling system includes an aspiration means for delivering air into the particle detector at an aspiration flow rate, the aspiration flow rate determining the sample flow rate from the at least one upstream sampling point into a sampling pipe of the air sampling system.

4. An air sampling system in accordance with claim 1, wherein the air sampling system further includes a sensor for determining air flow at said location downstream.

5. An air sampling system in accordance with claim 4, wherein the air sampling system is configured to issue a fault signal in the event that a measured air flow is not at the predetermined flow rate at the location downstream.

6. An air sampling system in accordance with claim 1, wherein the body includes a passage between the apertures and the outlet.

7. An air sampling system in accordance with claim 1, wherein there are three of said apertures.

8. An air sampling system in accordance with claim 7, wherein the apertures are spaced at 120 degree intervals about the central axis of the cylindrical body.

9. An air sampling system in accordance with claim 1, wherein the at least one upstream sampling point includes a weather shield configured to provide protection from water ingress or hole blockage due to rain or snow.

10. A particle detection system comprising:
a particle detector; and
an air sampling system in fluid communication with the particle detector, the sampling system having:
   at least one sampling pipe configured to deliver air to a particle detector;
   the sampling pipe connected to a plurality of sampling points for drawing air into the sampling pipe;
   the sampling system being configured to have a flow of air at a predetermined flow rate at a location downstream from at least some of the sampling points;
   wherein at least one of the sampling points is upstream from the location downstream and has a generally cylindrical body that is closed on a bottom end, the body having a plurality of equally-sized apertures equally spaced about a central axis of the cylindrical body in a spatial arrangement each for drawing an air sample from an ambient environment into the body, and an outlet for delivering the sampled air, at a predetermined sample flow rate, from the body into the at least one sampling pipe, the spatial arrangement of equally-sized apertures balancing air flowing into the body such that the effect of a change in flow rate into one of the apertures caused by the presence or absence of ambient flow of air about the at least one upstream sampling point is at least partly matched by changes in flow in at least one of the other apertures, delivering the sampled air at the outlet at the predetermined sample flow rate.

11. A particle detection system in accordance with claim 10, wherein the particle detector is a smoke detector and the particle detection system is a smoke detection system.

* * * * *

UNITED STATES PATENT AND TRADEMARK OFFICE
CERTIFICATE OF CORRECTION

PATENT NO. : 9,989,443 B2
APPLICATION NO. : 14/402748
DATED : June 5, 2018
INVENTOR(S) : Knox It is certified that error appears in the above-identified patent and that said Letters Patent is hereby corrected as shown below:

On the Title Page

Item (73), should read:
Garrett Thermal Systems Limited, Berkshire (UK)

Signed and Sealed this
Ninth Day of July, 2019

Andrei Iancu
*Director of the United States Patent and Trademark Office*